US011464893B2

(12) United States Patent
Pandolfini et al.

(10) Patent No.: US 11,464,893 B2
(45) Date of Patent: Oct. 11, 2022

(54) BLOOD RESERVOIR WITH BLOOD-HANDLING ASSEMBLY

(71) Applicant: Sorin Group Italia S.r.l., Milan (IT)

(72) Inventors: Clara Pandolfini, Roverbella (IT); Francesco Benatti, Concordia sulla Secchia (IT); Claudio Silvestri, Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 513 days.

(21) Appl. No.: 16/080,665

(22) PCT Filed: Feb. 29, 2016

(86) PCT No.: PCT/IB2016/051101
§ 371 (c)(1),
(2) Date: Aug. 29, 2018

(87) PCT Pub. No.: WO2017/149349
PCT Pub. Date: Sep. 8, 2017

(65) Prior Publication Data
US 2019/0060550 A1    Feb. 28, 2019

(51) Int. Cl.
*A61M 1/36*    (2006.01)
*A61M 60/113*    (2021.01)

(52) U.S. Cl.
CPC ........ *A61M 1/3632* (2014.02); *A61M 1/3666* (2013.01); *A61M 60/113* (2021.01); *A61M 2206/10* (2013.01)

(58) Field of Classification Search
CPC .............. A61M 1/3632; A61M 1/3666; A61M 1/1006; A61M 2206/10
See application file for complete search history.

(56) References Cited

U.S. PATENT DOCUMENTS

| | | | |
|---|---|---|---|
| 4,976,708 A * | 12/1990 | Oshiyama | A61M 1/3627 604/408 |
| 5,254,080 A * | 10/1993 | Lindsay | A61M 1/3632 604/405 |
| 5,849,186 A * | 12/1998 | Raneri | A61M 1/3632 210/489 |

(Continued)

FOREIGN PATENT DOCUMENTS

| | | |
|---|---|---|
| CN | 103648542 A | 3/2014 |
| EP | 2545948 A1 | 1/2013 |

(Continued)

OTHER PUBLICATIONS

International Preliminary Reporton Patentability received for PCT Patent Application No. PCT/IB2016/051101, dated Sep. 13, 2019, 10 pages.

(Continued)

*Primary Examiner* — Jessica R Arble
(74) *Attorney, Agent, or Firm* — Seager, Tufte & Wickhem LLP

(57) ABSTRACT

An apparatus includes a blood-flow-management assembly shaped to define a cylindrical aperture. The blood-flow-management assembly includes a blood collector having drainage holes configured to direct blood to a guide surface positioned below the blood collector. The guide surface may further include ribs that manage blood flow along the guide surface.

16 Claims, 4 Drawing Sheets

(56) References Cited

U.S. PATENT DOCUMENTS

| | | | |
|---|---|---|---|
| 6,083,392 A * | 7/2000 | Rigney | A47J 37/1271 210/477 |
| 6,287,270 B1 * | 9/2001 | Fini | A61M 1/3632 604/6.15 |
| 6,322,546 B1 * | 11/2001 | Steg | A61M 1/3627 604/319 |
| 10,213,541 B2 | 2/2019 | Silvestri et al. | |
| 2007/0293805 A1 * | 12/2007 | Ghelli | A61M 1/3627 604/6.15 |
| 2013/0017119 A1 * | 1/2013 | Silvestri | A61M 1/3666 422/45 |
| 2015/0196703 A1 | 7/2015 | Silvestri et al. | |

FOREIGN PATENT DOCUMENTS

| | | |
|---|---|---|
| JP | 05-181996 A | 7/1993 |
| JP | 2008-000597 A | 1/2008 |
| JP | 2013-017806 A | 1/2013 |
| WO | 2015/045681 A1 | 4/2015 |

OTHER PUBLICATIONS

International Search Report and Written Opinion received for PCT Patent Application No. PCT/IB2016/051101, dated Nov. 8, 2016, 12 pages.

* cited by examiner

BLOOD RESERVOIR WITH BLOOD-HANDLING ASSEMBLY

CROSS-REFERENCE TO RELATED APPLICATION

This application is a national stage application of PCT/IB2016/051101, filed Feb. 29, 2016, which is herein incorporated by reference in its entirety.

TECHNICAL FIELD

The present disclosure relates generally to blood reservoirs for oxygenators used in blood perfusion systems.

BACKGROUND

Blood perfusion involves encouraging blood through the vessels of the body. For such purposes, blood perfusion systems typically include the use of one or more pumps in an extracorporeal circuit that is interconnected with the vascular system of a patient. Many surgical procedures require or prefer temporary cessation of the heart to create a still operating field. Such procedures may thus rely upon a cardiopulmonary bypass (CPB) perfusion system that temporarily replaces the function of the heart and lungs. Examples of such procedures include the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs, respectively.

More specifically, in cardiopulmonary bypass procedures, oxygen-poor blood (i.e., venous blood) is gravity-drained or vacuum-suctioned from a large vein entering the heart or another major vein in the body (e.g., femoral) and is transferred through a venous line in the extracorporeal circuit. The venous blood is pumped to an oxygenator that provides for oxygen transfer to the blood. Oxygen may be introduced into the blood by, for example, transfer across a membrane. Concurrently, carbon dioxide is removed across the membrane. The oxygenated blood is filtered and then returned through an arterial line to the aorta, femoral, or other artery.

In many cases, an extracorporeal blood circuit includes a blood reservoir that can be used to collect, filter and de-aerate blood from a variety of different sources. For example, a blood reservoir may receive one or more of venous blood from a large vein, vent blood that is collected within the heart, and cardiotomy or suction blood that is collected from outside the heart but within the surgical field.

SUMMARY

The present disclosure relates to blood reservoirs that may be used in combination with other elements such as a heart lung machine, oxygenator, heat exchanger, arterial filter and the like to form an extracorporeal blood circuit. Blood reservoirs, as will be described in greater detail, may be configured to receive, filter and store blood from a number of sources including vent blood (from within the heart), venous blood (from a major vein), purge blood (from a sampling or purge line), and cardiotomy or suction blood (from within the surgical field). Blood reservoirs may also receive air along with blood from the various sources. Air can cause blood to bubble and create foam. Foam can increase activation in blood and can hinder the volume and flow of blood through filters. Certain embodiments of the present disclosure are accordingly directed to systems, methods, and devices that mitigate the effects of bubbles and foam in a blood reservoir.

In Example 1, a blood reservoir includes a housing having a venous inlet and a vent inlet. The reservoir also includes a venous tube in fluid communication with the venous inlet and at least one vent tube in fluid communication with the vent inlet for directing blood to a blood-handling assembly. The blood-handling assembly surrounds a portion of the venous tube and is positioned within the housing. The blood-handling assembly includes a blood-collection chamber that defines drainage holes for directing blood to a guide surface.

In Example 2, the blood reservoir of Example 1, wherein the guide surface includes ribs protruding from the guide surface and configured to manage blood flow along the guide surface.

In Example 3, the blood reservoir of Example 2, wherein at least one of the ribs includes a top section and two legs extending from the top section in a downward direction.

In Example 4, the blood reservoir of any of Examples 1-3, wherein the blood-handling assembly is shaped to define a cylindrical aperture that surrounds at least a portion of the venous tube.

In Example 5, the blood reservoir of any of Examples 1-4, wherein the drainage holes are sized to stop foam from entering an area of the blood reservoir below the blood-collection chamber.

In Example 6, the blood reservoir of any of Examples 1-5, wherein the drainage holes form a circular array in the blood-collection chamber.

In Example 7, the blood reservoir of any of Examples 1-6, further comprising a defoamer surrounding the blood-collection chamber.

In example 8, the blood reservoir of any of Examples 1-7, wherein the blood-handling assembly is dimensioned to allow contact of blood with the defoamer only when blood foam is present in a filter assembly.

In Example 9, the blood reservoir of any of Examples 1-8, wherein the blood-collection chamber is bowl shaped.

In Example 10, the blood reservoir of any of Examples 1-9, further comprising a filter assembly disposed within the housing and shaped to define an internal cavity, and wherein the blood-handling assembly is positioned within the internal cavity.

In Example 11, the blood reservoir of any of Examples 1-10, further including a releasable barrier configured and arranged to separate activated and non-activated sections of the blood reservoir.

In Example 12, the blood reservoir of Example 11, wherein the blood-handling assembly is positioned in the non-activated blood section.

In Example 13, an apparatus includes a blood-flow-management assembly shaped to define a cylindrical aperture for receiving a venous blood tube. The assembly includes a blood collector having drainage holes configured to direct blood to a guide surface positioned below the blood collector.

In Example 14, the apparatus of Example 13, wherein the guide surface includes ribs protruding from the surface to manage blood flow along the guide surface.

In Example 15, the apparatus of Example 14, wherein the ribs and guide surface are integral with each other.

In Example 16, the apparatus of any of Examples 14-15, wherein at least one of the ribs includes a top section and two legs extending from the top section in a downward direction.

In Example 17, the apparatus of Example 16, wherein a distance between the legs increases as the legs extend in the downward direction.

In Example 18, the apparatus of any of Examples 13-17, wherein blood collector is bowl shaped.

In Example 19, the apparatus of any of Examples 13-18, wherein the drainage holes form a circular array in the blood collector.

In Example 20, the apparatus of any of Examples 13-19, wherein the guide surface defines an outer diameter, and wherein an outer diameter at a top of the guide surface near the blood-collection bowl is smaller than an outer diameter of the guide surface at a bottom of the guide surface.

In Example 21, the apparatus of any of Examples 13-20, wherein the drainage holes are configured to stop foam from passing through the drainage holes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
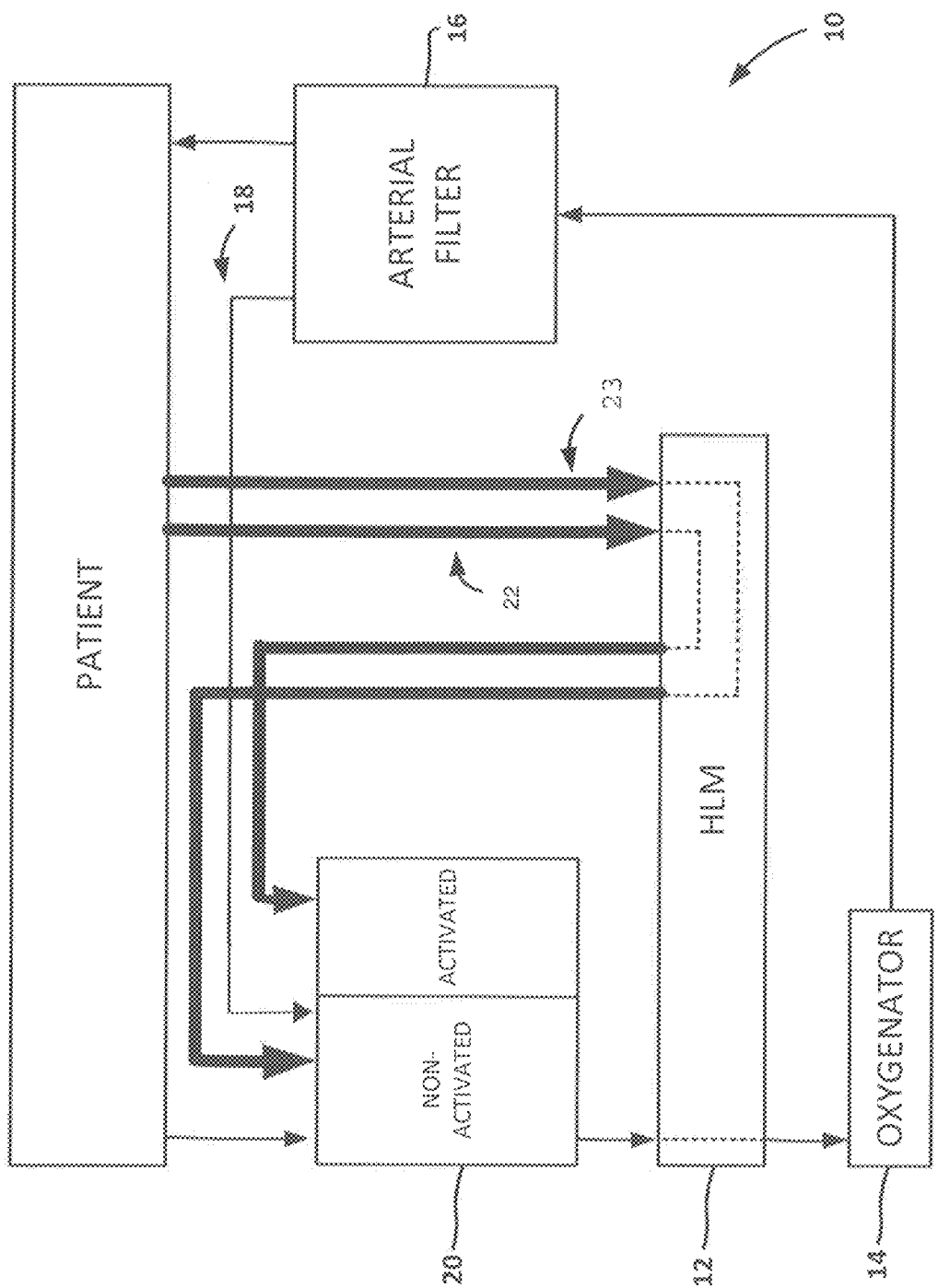
FIG. 1 shows a schematic illustration of an extracorporeal blood circuit in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an extracorporeal blood circuit 10. As illustrated, the extracorporeal blood circuit 10 includes a heart-lung machine (HLM) 12, oxygenator 14, arterial filter 16 with purge line 18, blood reservoir 20, and sucker 22 and vent 23 lines. The HLM 12 is in fluid communication with a patient and as such can receive blood from the patient and can return blood and other fluids to the patient 22. The purging line 18 permits blood to be withdrawn from the extracorporeal blood circuit 10 for lab work and/or additional testing done in the surgical arena. Blood through the purging line 18 may flow into the blood reservoir 20. The sucker 22 and vent 23 lines allow blood to be collected from heart cavities and from a surgical field, respectively, to pump blood into the reservoir 20 via the HLM 12.

Figure 2:
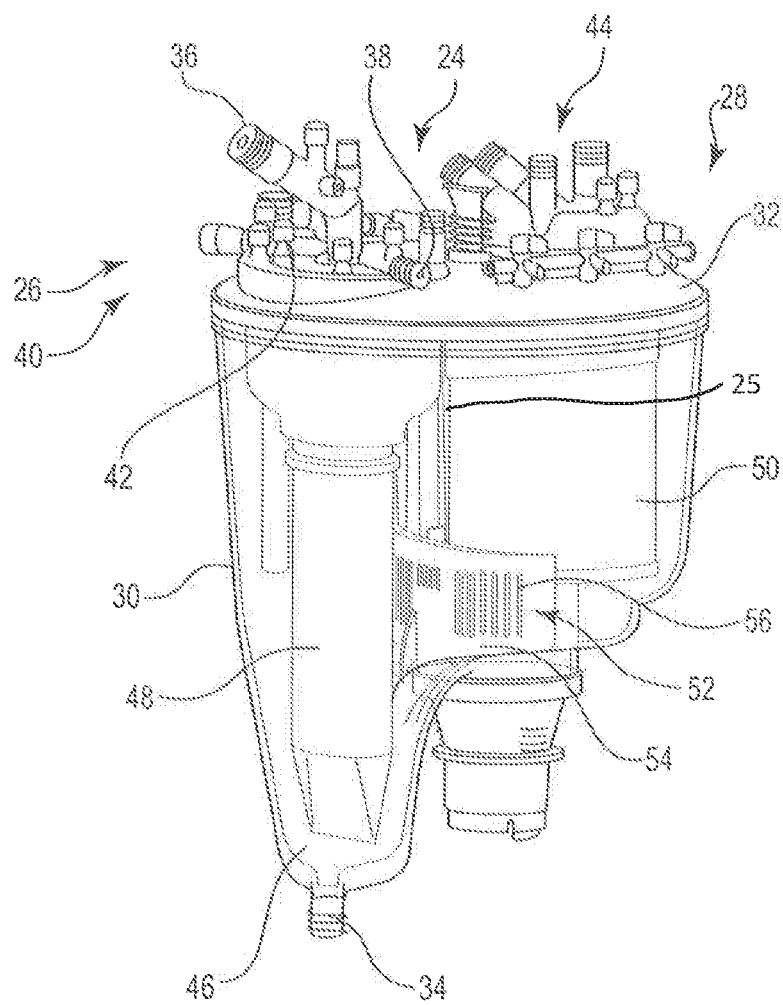
FIG. 2 shows a partially cross-sectioned perspective view of a blood reservoir in accordance with certain embodiments of the present disclosure.

FIG. 2 is a partially cross-sectioned perspective view of a blood reservoir 24 that may be used as the blood reservoir 20 in the extracorporeal blood circuit 10 of FIG. 1. The blood reservoir 24 includes a clean (i.e., non-activated) blood section 26 and a dirty (i.e., activated) blood section 28. "Clean" and "dirty" are relative terms pertaining to an expected level of solid particles or air bubbles within the blood entering each section. For example, vent blood and venous blood, which are usually fairly clean, may be processed within the non-activated section 26, while suction blood, which tends to contain relatively more debris, may be processed within the activated section 28.

As shown in FIG. 2, the blood reservoir 24 includes a housing 30 and a cover 32. A number of blood inlets, as will be described, extend through or are otherwise disposed within the cover 32. The housing 30 includes a blood outlet 34 that may, in some embodiments, be in fluid communication with the HLM 12. The housing 30 tapers to a bottom 46. The cover 32 accommodates a venous inlet port 36, one or more vent inlet ports 38 (only one is visible in this view) and a purgers inlet 40 having one or more purgers ports 42. The cover 32 also accommodates a suction inlet 44. In some embodiments, one or more of the venous inlet port 36, the vent inlet port(s) 38, the purgers inlet 40 or the suction inlet 44 may pass through the cover 32 such that they can rotate relative to the cover 32.

As shown, the non-activated section 26 includes a filtering assembly 48, while the activated section 28 includes a filtering/defoaming assembly 50. The filtering assembly includes a filter, which is disposed within the housing 30 and which can be shaped to define a cavity in which the features of FIGS. 3 and 4 can be positioned. The blood reservoir 24 includes a movable or releasable valve 25 that, when in place, keeps blood within the activated section 28 from entering the non-activated section 26. In some cases, there may be a need for more blood than is available from the non-activated section 26 and thus the valve 25 may be lifted, rotated or otherwise moved to permit blood to pass from the activated section 28 to the non-activated section 26.

In some embodiments, the housing 30 may include a shield 52 that directs blood from the activated section 28 towards the bottom 46. The shield 52 may be shaped and positioned to minimize turbulence within the blood flow. In some embodiments, as illustrated, the shield 52 may include a frame portion 54 and a porous media portion 56. The frame portion 54 supports the porous media portion 56 and helps to anchor the shield 52 within the housing 30. The porous media portion 56 slows blood passing through the shield 52. While relative blood levels may vary during use in the non-activated section 26 and the activated section 28 (when the valve is closed), in some operating conditions, the blood level within the non-activated section 26 may be relatively lower than the blood level within the activated section 28. In some operating conditions, the blood level within the non-activated section 26 may instead be higher than the blood level within the activated section 28.

Figure 3:
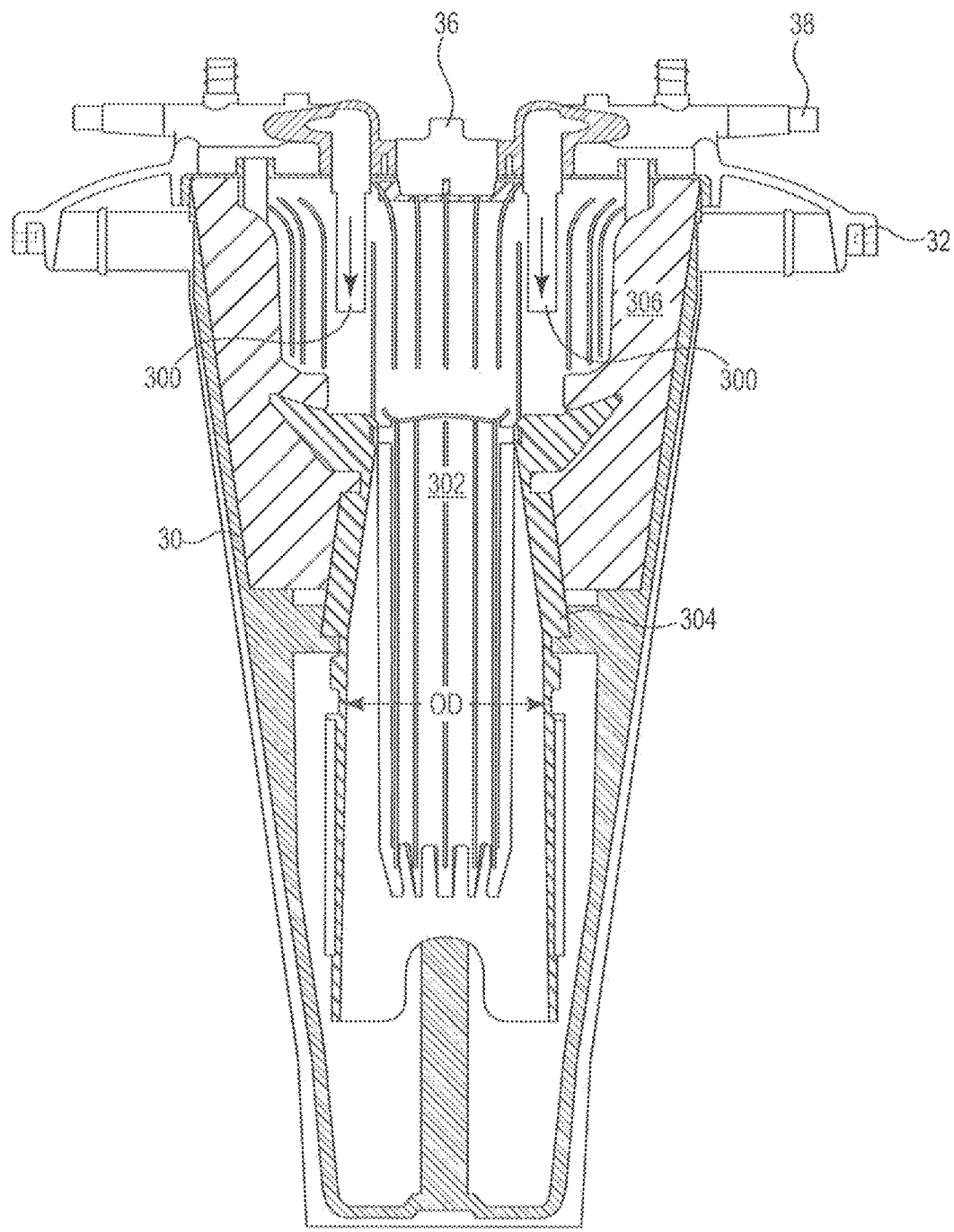
FIG. 3 shows a partially cross-sectioned perspective view of a venous filter portion of a blood reservoir in accordance with certain embodiments of the present disclosure.

FIG. 3 shows a partially cross-sectioned perspective view of a non-activated portion of a blood reservoir. Vent blood enters the reservoir through the cover 32 via vent inlet ports 38 that are in fluid communication with vent tubes 300. Venous blood enters the reservoir through the cover 32 via a venous inlet port 36 that is in fluid communication with a venous tube that extends along a frame 302.

Vent blood exits the vent tubes 300 and collects in a blood-handling assembly 304, which is partially surrounded by defoamer 306. Because vent tubes 300 terminate above a level at which blood collects, the blood reservoir of the present disclosure can handle situations where 100% air enters into the reservoir through the vent tubes 300—a capability not present in prior art assemblies.

Figure 4:
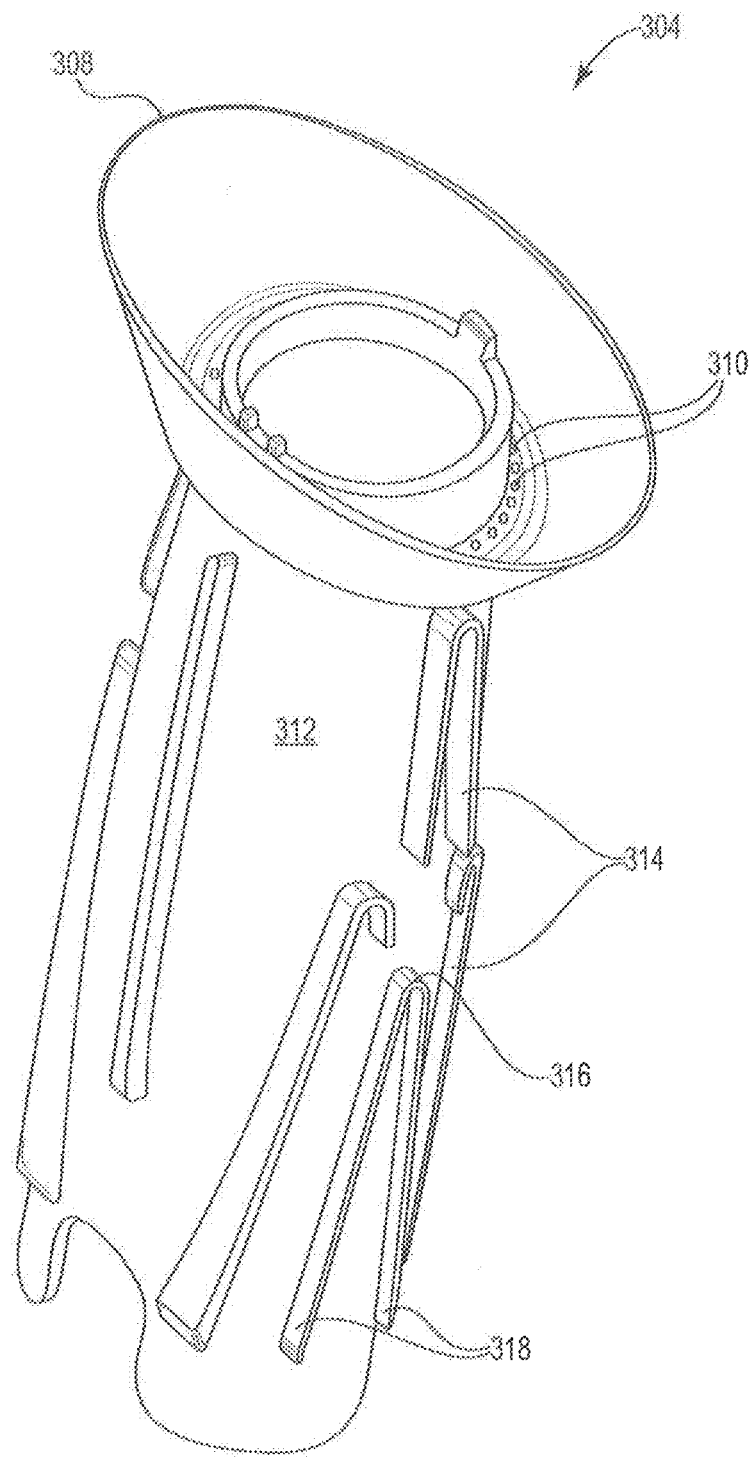
FIG. 4 shows a perspective view of a blood-handling assembly of a blood reservoir in accordance with certain embodiments of the present disclosure.

As shown in more detail in FIG. 4, blood-handling assembly 304 includes blood-collection chamber 308 that includes drainage holes 310 positioned at the base of the chamber 308. The chamber 308 is shown as being bowl shaped but other suitable shapes can be used. Positioned below the chamber 308 is a guide surface 312 that has multiple ribs 314 protruding from the surface. The blood-handling assembly 304 forms a central aperture for at least a part of the central venous tube to extend through such that the blood-handling assembly surrounds the venous tube. Although the blood-handling assembly 304 is shown as being a single, integral piece, the assembly can be made in separate pieces, then assembled together.

After entering the collection chamber 308, blood drains through the drainage holes 310 and slides down the guide surface 312. The drainage holes 310 are sized to mitigate foam from entering an area of the reservoir below the collection chamber 308. Drainage holes 310 are also sized to accept and facilitate blood flowing from vent tubes 300. Although the drainage holes are shown as being positioned in a circular array around the central aperture, other suitable configurations can be used. Should foam generate in or above an area of the collection chamber 308, defoamer 306 can dissolve the foam once the foam contacts the defoamer 306. A diameter of the blood-handling assembly 304 at the guide surface 312 is shown as increasing in a downward direction along the guide surface 304, which assists with slowing the flow of blood. The ribs 314 also act to slow the flow of blood sliding down the guide surface 312 to mitigate blood splashing into a bottom of the reservoir. Mitigating splashing mitigates the creation of bubbles and foam in the reservoir. As discussed above, foam can increase activation in blood and slow flow through filters resulting in "blood holdup" within the blood reservoir. Some of the ribs 314 are shown in FIG. 4 to have a top section 316 and legs 318 extending in a downward direction along the guide surface 312.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A blood reservoir comprising:
    a housing having a venous inlet and a vent inlet;
    a venous tube in fluid communication with the venous inlet;
    at least one vent tube in fluid communication with the vent inlet for directing blood to a blood-handling assembly that surrounds a portion of the venous tube; and
    the blood-handling assembly positioned within the housing and including a blood-collection chamber defining drainage holes for directing blood to a guide surface, the guide surface including ribs protruding from the guide surface and configured to manage blood flow along the guide surface, wherein at least one of the ribs includes a top section and two legs extending from the top section in a downward direction.

2. The blood reservoir of claim 1, wherein the blood-handling assembly is shaped to define a cylindrical aperture that surrounds at least a portion of the venous tube.

3. The blood reservoir of claim 1, wherein the drainage holes are sized to prevent foam from entering an area of the blood reservoir below the blood-collection chamber.

4. The blood reservoir of claim 1, wherein the drainage holes form a circular array in the blood-collection chamber.

5. The blood reservoir of claim 1, further comprising:
    a defoamer surrounding the blood-collection chamber.

6. The blood reservoir of claim 5, wherein the blood-handling assembly is dimensioned to allow contact of blood with the defoamer only when blood foam is present in or above the blood-collection chamber.

7. The blood reservoir of claim 1, wherein the blood-collection chamber is bowl shaped.

8. The blood reservoir of claim 1, further comprising:
    a filter assembly disposed within the housing and shaped to define an internal cavity, wherein the blood-handling assembly is positioned within the internal cavity.

9. The blood reservoir of claim 1, further comprising:
    a releasable valve configured and arranged to separate activated and non-activated sections of the blood reservoir.

10. The blood reservoir of claim 9, wherein the blood-handling assembly is positioned in the non-activated blood section.

11. An apparatus comprising:
    a blood-flow-management assembly shaped to define a cylindrical aperture for receiving a venous blood tube, wherein the assembly includes a blood collector having a plurality of drainage holes forming a circular array in the blood collector, the plurality of drainage holes configured to direct blood to a guide surface positioned below the blood collector, wherein an upper extent of the cylindrical aperture is located above the plurality of drainage holes, wherein the guide surface includes ribs protruding from the surface, wherein at least one of the ribs includes a top section and two legs extending from the top section in a downward direction.

12. The apparatus of claim 11, wherein the ribs and guide surface are integral with each other.

13. The apparatus of claim 11, wherein a distance between the legs increases as the legs extend in the downward direction.

14. The apparatus of claim 11, wherein the blood collector is bowl shaped.

15. The apparatus of claim 11, wherein the guide surface defines an outer diameter, and wherein an outer diameter at a top of the guide surface near the blood collector is smaller than an outer diameter of the guide surface at a bottom of the guide surface.

16. The apparatus of claim 11, wherein the drainage holes are configured to stop foam from passing through the drainage holes.

* * * * *